United States Patent [19]

Takuma et al.

[11] Patent Number: 5,698,697
[45] Date of Patent: Dec. 16, 1997

[54] 2-CYANOPIPERAZINE AND METHOD OF PRODUCING THE SAME

[75] Inventors: Yuki Takuma; Yuzo Kasuga; Takeki Miyazaki; Yuji Mizuho; Ken Okamoto, all of Fukuoka, Japan

[73] Assignee: Mitsubishi Chemical Corporation, Toyko, Japan

[21] Appl. No.: 683,370

[22] Filed: Jul. 18, 1996

[30] Foreign Application Priority Data

| Jul. 19, 1995 | [JP] | Japan | HEI 7-182857 |
| Oct. 12, 1995 | [JP] | Japan | HEI 7-264059 |
| Oct. 12, 1995 | [JP] | Japan | HEI 7-264060 |

[51] Int. Cl.$^6$ ............................................. C07D 24/04
[52] U.S. Cl. ..................................... 544/402; 544/390
[58] Field of Search .................................... 544/402

[56] References Cited

U.S. PATENT DOCUMENTS

| 4,925,901 | 5/1990 | Bertram et al. | 525/482 |
| 5,612,484 | 3/1997 | Askin et al. | 544/360 |

OTHER PUBLICATIONS

Rossen, et al., "Asymmetric Hydrogenation of Tetrahydropyrazines: Synthesis of (S)—Piperazine–2–tert–butylcarboxamide, an Intermediate in the Preparation of the HIV Protease Inhibitor Indinavir", Tetrahedron Letters, vol. 36, No. 36, pp. 6419–6422, 1995.

*Primary Examiner*—Emily Bernhardt
*Attorney, Agent, or Firm*—Dilworth & Barrese

[57] ABSTRACT

2-Cyanopiperazine represented by the following formula (1):

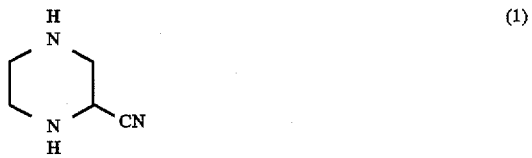

or a salt thereof.

The 2-cyanopiperazine can be produced by reacting a 2-halogenoacrylonitrile with ethylenediamine or by reacting a 2,3-dihalogenopropionitrile with ethylenediamine.

The 2-cyanopiperazine is useful as an intermediate for medicaments, agricultural chemicals, etc., and optically active N-tert-butyl-2-piperazine carboxamide, which is useful as an intermediate in preparation of the HIV protease inhibitor indinavir, can be easily produced using the 2-cyanopiperazine.

5 Claims, No Drawings

2-CYANOPIPERAZINE AND METHOD OF PRODUCING THE SAME

FIELD OF THE INVENTION

The present invention relates to 2-cyanopiperazine represented by the following formula (1):

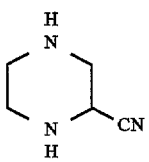
(1)

and a production method thereof. 2-Cyanopiperazine is a novel compound and is useful as an intermediate for medicaments, agricultural chemicals, etc.

Also, the present invention relates to N-tert-butyl-2-piperazine carboxamide derived from the 2-cyanopiperazine represented by the formula (1) as starting material. The optically active N-tert-butyl-2-piperazine carboxamide is also a useful compound as an intermediate for medicaments, for example, as an intermediate for preparation of the protease inhibitor indinavir.

BACKGROUND OF THE INVENTION

Piperazine-2-tert-butylcarboxamide represented by the following formula (2):

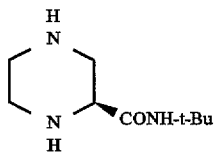
(2)

is an intermediate in preparation of the HIV protease inhibitor indinavir "chiral (S)-N-Boc-piperazine MK-639.

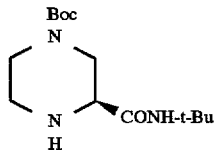
(3)

In the formula, Boc represents a tert-butylcarbonyl group.

Tetrahedron Letters, vol. 36, pages 6419–6422, 1995 describes Merck HIV protease inhibitor indinavir represented by the following formula (5) is constructed by coupling an epoxide represented by the following formula (4) with (S)-2-tert-butylcarboxamide-4-tert-butoxycarbonylpiperazine represented by the formula (3) as shown in the following reaction diagram.

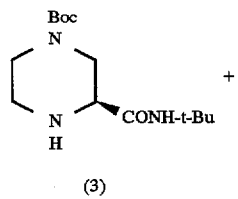
(3)

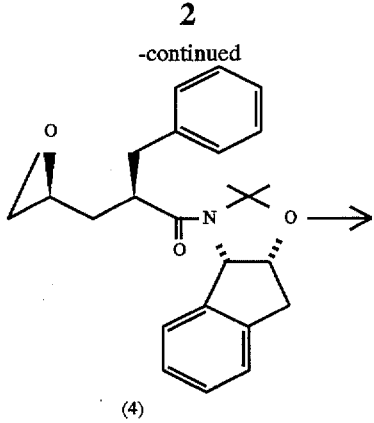
(4)

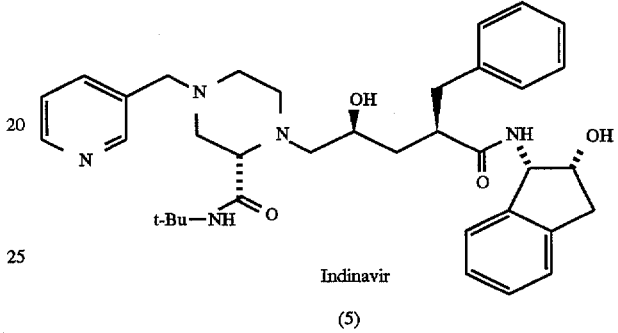

Indinavir
(5)

(S)-2-tert-butylcarboxamide-4-tert-butoxycarbonyl-piperazine represented by the formula (3) is obtained by the following procedure.

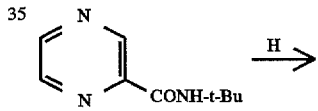
(6)

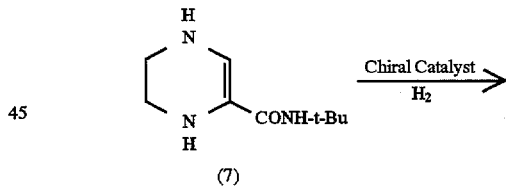
(7)

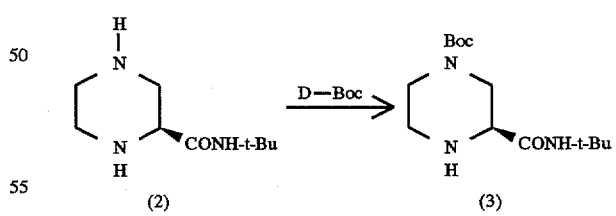
(2)   (3)

In this diagram, D-Boc represents di-tert-butyl-di-carbonate.

N-tert-butyl-2-pyrazine carboxamide represented by the formula (6) is obtained by reacting cyanopyrazine represented by the following formula (8) with tert-butyl alcohol in the presence of sulfonic acid (see JP-A-7-145153, the term "JP-A" as used herein means an "unexamined published Japanese patent application).

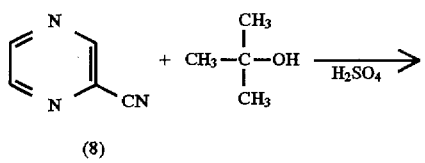

(8)

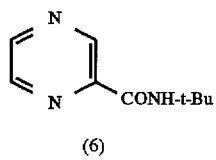

(6)

Also, hitherto, in regard to the production method of N-tert-butyl-2-piperazine carboxamide represented by the following formula (2), the only method of hydroreducing N-tert-butyl-2-pyrazine carboxamide represented by the formula (6) in the presence of a platinum oxide catalyst or an LiAlH$_4$ catalyst under the conditions of 50° C. and 100 atms is reported as described in JP-A-1-117869.

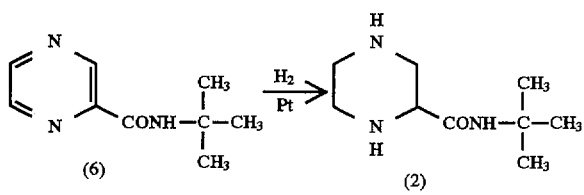

However, the foregoing method has an industrial disadvantage since in this method, an expensive platinum oxide catalyst is required and also high-pressure equipment enduring a pressure of 100 atms is required, and hence a method of producing N-tert-butyl-2-piperazine carboxamide with low cost and with good yield has been desired.

SUMMARY OF THE INVENTION

It has now been discovered that N-tert-butyl-2-piperazine carboxamide represented by the formula (2) described above can be produced without using such an expensive catalyst, by using instead 2-cyanopiperazine of the present invention as the starting material.

Thus, an object of the present invention is to provide the novel compound, 2-cyanopiperazine represented by the formula (1) described above, which is useful as an intermediate for medicaments, agricultural chemicals, etc.

Other object of the present invention is to provide a method of producing said 2-cyanopiperazine represented by the formula (1).

Another object of the present invention is to provide N-tert-butyl-2-piperazine carboxamide represented by the formula (2) described above, which is a useful intermediate for preparation of the HIV protease inhibitor indinavir, obtained from using 2-cyanopiperazine represented by the formula (1) of the present invention.

That is, according to the 1st aspect of the present invention, there is provided 2-cyanopiperazine represented by the formula (1) described above.

Also, according to the 2nd aspect of the present invention, there is provided a method of producing 2-cyanopiperazine, which comprising reacting an ethylenediamine with a 2-halogenoacrylonitrile represented by following formula (9):

wherein X represents a halogen atom.

According to the 3rd aspect of the present invention, there is further provided other method of producing 2-cyanopiperazine represented by the formula (1) described above, which comprises reacting an ethylenediamine with a 2,3-dihalogenopropionitrile represented by following formula (10):

wherein X represents a halogen atom.

Furthermore, according to the 4th aspect of the present invention, there is provide N-tert-butyl-2-piperazine carboxamide represented by the formula (2) described above obtained by reacting 2-cyanopiperazine represented by the formula (1) described above and tert-butyl alcohol in the presence of an acid.

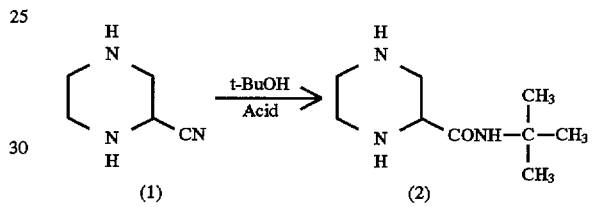

DETAILED DESCRIPTION OF THE INVENTION

The present invention is described in detail below.

First, the method of the 2nd aspect of the present invention, that is, the method of producing 2-cyanopiperazine of this invention represented by the formula (1) by reacting a 2-halogenoacrylonitrile represented by the formula (9) described above and ethylenediamine is as follows.

The reaction can be carried out without solvent but is preferably carried out in an inert solvent.

As the inert solvents, ethers such as tetrahydrofuran, diethyl ether, dibutyl ether, etc.; alcohols such as methyl alcohol, ethyl alcohol, butyl alcohol, etc.; (halo)aromatic hydrocarbons such as benzene, toluene, xylene, chlorobenzene, dichlorobenzene, etc.; aliphatic or alicyclic hydrocarbons such as hexane, heptane, cyclohexane, etc.; halogenated hydrocarbons such as dichloromethane, dichloroethane, chloroform, carbon tetrachloride, etc.; acetonitrile; water; etc., are used. Preferably, tetrahydrofuran, toluene, dichloromethane, dichloroethane, chloroform, etc., are used. The solvent is usually used in an amount 1 to 20 times by volume as much as the amount of the 2-halogenoacrylonitrile.

When the reaction of this invention is carried out without solvent, it is preferred to use an excessive amount of ethylenediamine so that a part of ethylenediamine functions as a solvent.

In the reaction of the present invention, since hydrohalogenic acid is formed, a base is used in the reaction system to capture the acid. As the base, amines such as triethylamine, pyridine, dimetylaniline, etc., sodium hydroxide, potassium hydroxide, sodium carbonate, etc. are used and the amount of the base to be used is from 1 to 3 molar equivalents, and preferably from 1 to 2 molar equivalents to one mole of the 2-halogenoacrylonitrile.

In a preferred embodiment of the present invention, ethylenediamine is used excessively so that a part of ethylenediamine functions as a base. The amount of ethylenediamine to be used is usually determined in the range of from 1 to 10 moles per mole of the 2-halogenoacrylonitrile depending on the presence or absence of a base and a solvent being used together. When a solvent is used but the base is not used together with ethylenediamine, it is preferred to use from 1.5 to 2 moles of ethylenediamine to one mole of the 2-halogenoacrylonitrile.

The reaction of the 2-halogenoacrylonitrile and ethylenediamine is usually carried out at a temperature of from −20° C. to +100° C. but from the point of view of the reaction rate and the yield, it is preferred to carry out the reaction at a temperature of from 20° C. to 60° C.

The reaction pressure may be such that the reaction system keeps its liquid phase, and the reaction is usually carried out at normal pressure but, if desired, the reaction may be carried out under a reduced pressure or under positive pressure.

The reaction can be most simply carried out by charging an inert solvent, ethylenediamine, and a base in a reaction vessel and adding dropwise the 2-halogenoacrylonitrile to the mixture under stirring.

Since the reaction is an exothermic reaction, if desired, the reaction system may be appropriately cooled.

The separation and the purification of 2-cyanopiperazine thus formed from the reaction mixture can be carried out by any of conventional separation and purification methods. For example, by-produced salts are precipitated from the reaction mixture and removed by a filtration, and an acid is added to the filtrate to precipitate 2-cyanopiperazine as the acid-addition salt, which is collected by filtration. As the acid to be added in this case, an inorganic acid such as hydrochloric acid, sulfuric acid, hydrobromic acid, etc., is preferred and the amount of the acid is from 1 to 3 molar equivalents, preferably from 1 to 1.5 molar equivalent to one mole of 2-cyanopiperazine.

The acid-addition salt of 2-cyanopiperazine is dissolved in water to form an aqueous solution thereof, then by neutralizing the aqueous solution with sodium hydroxide, etc., 2-cyanopiperazine is liberated. By extracting the product with an organic solvent such as ethyl acetate, etc., and then removing the organic solvent by evaporation, 2-cyanopiperazine can be isolated.

Also, as another method of producing 2-cyanopiperazine according the 3rd aspect of the present invention, by reacting a 2,3-dihalogenopropionitrile represented by the formula (3) described above and ethylenediamine, 2-cyanopiperazine can be produced with a high yield. In the formula (3), X is preferably chlorine, bromine or iodine.

The reaction can be carried out without solvent but is preferably carried out in an inert solvent. As the inert solvent, the inert solvents as described in the reaction described above can be similarly used. Among these inert solvents, tetrahydrofuran, toluene, dichloromethane, dichloroethane, chloroform, etc., are preferably used. The solvent is usually used in an amount 1 to 20 times by volume as much as the amount of the 2,3-dihalogenopropionitrile.

When the reaction is carried out without solvent, it is preferred that ethylenediamine is excessively used so that a part of ethylenediamine functions as solvent.

In the reaction, since hydrohalogenic acid is formed, a base is used in the reaction system to capture the acid. As the base, amines such as triethylamine, pyridine, dimethylaniline, etc., sodium hydroxide, potassium hydroxide, sodium carbonate, etc. are used and the amount of the base to be used is from 2 to 4 molar equivalents, and preferably from 2 to 3 molar equivalents to one mole of the 2,3-dihalogenopropionitrile.

In a preferred embodiment of the present invention, ethylenediamine, which is a starting material, is excessively used so that a part of ethylenediamine functions as the base. Usually, the amount of ethylenediamine to be used is determined in the range of from 1 to 20 moles per mole of the 2,3-dihalogenopropionitrile depending on the presence or absence of the base and the solvent being used. When a solvent is used but the base is not used together with ethylenediamine, it is preferred to use from 2 to 10 moles of ethylenediamine per mole of the 2,3-dihalogenopropionitrile.

The reaction of the 2,3-dihalogenopropionitrile and ethylenediamine is usually carried out at a temperature of from −20° C. to +100° C. but from the point of view of the reaction rate and the yield, it is preferred to carry out the reaction at a temperature of from 20° C. to 60° C.

The reaction pressure may be such that the reaction system keeps the liquid phase and usually the reaction is carried out at normal pressure but, if desired, the reaction may be carried out under a reduced pressure or under positive pressure.

The reaction can be most simply carried out by charging an inert solvent, ethylenediamine, and the base in a reaction vessel and adding dropwise the 2,3-dihalogenopropionitrile to the mixture under stirring. Since the reaction is an exothermic reaction, if desired, the reaction system is appropriately cooled.

For separating and purifying 2-cyanopiperazine from the reaction mixture, 2-cyanopiperazine can be isolated by the same separation and purification method as shown in the production method of 2-cyanopiperazine in the 2nd aspect of the present invention described above.

For producing N-tert-butyl-2-piperazine carboxamide represented by the formula (2) described above using 2-cyanopiperazine of this invention as the starting material, 2-cyanopiperazine represented by the formula (1) is reacted with tert-butyl alcohol in the presence of an acid as shown in the following reaction scheme.

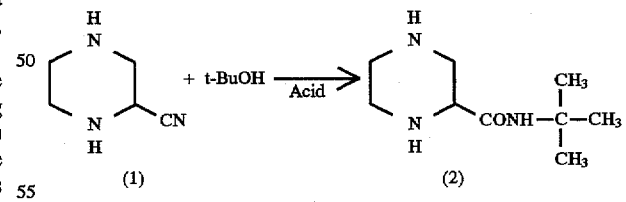

Practically, the reaction is carried out by adding dropwise tert-butyl alcohol to the mixture of an acid and 2-cyanopiperazine, by adding dropwise 2-cyanopiperazine to the mixture of an acid and tert-butyl alcohol, or by adding dropwise an acid to the mixture of 2-cyanopiperazine and tert-butyl alcohol.

As the acid, sulfuric acid, orthophosphoric acid, formic acid, Lewis acid, etc., can be used. In particular, sulfuric acid is preferred.

In the case of using sulfuric acid, the reaction may proceed using diluted sulfuric acid of about 10% in concentration but the use of sulfuric acid of a concentration of from 50% to 90% is preferred from the point of the yield. The amount of the acid to be used is preferably at least the theoretical amount necessary for neutralizing the amino group of 2-cyanopiperazine and decomposing the cyano group of 2-cyanopiperazine by addition of alcohol.

For example, in the case of sulfuric acid, sulfuric acid is used in an amount of at least 2 moles, and preferably from 2 to 20 moles to one mole of 2-cyanopiperazine. The amount of sulfuric acid to be used is most preferably from 5 to 15 moles for obtaining the desired product with a high yield. When the amount of sulfuric acid to be used is less than 2 moles to one mole of 2-cyanopiperazine, the yield for the product is low.

Also, it is preferred that the amount of tert-butyl alcohol to be used is at least on the equimolar basis with regard to 2-cyanopiperazine and from the economical point, the appropriate amount is from about 1 to 2 moles.

The reaction temperature is usually from 0° C. to 80° C., and preferably from 0° C. to 50° C.

In each of the foregoing reactions, 2-cyanopiperazine, tert-butyl alcohol, or the acid is added dropwise at the foregoing temperature for a time of from 0.5 hour to 5 hours and thereafter, by keeping the reaction system for a time of from 0 to 10 hours at the same temperature, the reaction is completed.

Then, N-tert-butyl-2-piperazine carboxamide formed by the reaction can be isolated by neutralizing the reaction mixture by the addition of an alkali, extracting the reaction mixture with an organic solvent, and then removing the organic solvent from the extract by distillation. Also, in another method, N-tert-butyl-2-piperazine carboxamide can be obtained by adding dropwise the reaction mixture to a water-soluble organic solvent and precipitating N-tert-butyl-2-piperazine carboxamide as the acid-addition salt thereof.

In addition, to obtain optically active N-tert-butyl-2-piperazine carboxamide represented by the formula (2) described above by optically resolving the racemic form of the carboxamide, diastereomer salts are formed with various optically active α-oxycarboxylic acid and are resolved by virtue of the difference of solubility of two diastereomer salts. For example, a method of using optically active lactic acid, malic acid, or tartaric acid as a resolving agent is known as described in JP-A-8-3145.

By optically resolving N-tert-butyl-2-piperazine carboxamide, which is the racemic modification, using an optically active N-acylamino acid as a resolving agent, optically active N-tert-butyl-2-piperazine carboxamide can be produced with a higher yield.

Examples of such an optically active N-acylamino acid-type resolving agent are N-benzyloxycarbonyl-L-phenylalanine (hereinafter, referred to as Z-L-Phe) and N-benzyloxycarbonyl-L-aspartic acid (hereinafter, referred to as Z-L-Asp). As each of these optically active N-acylamino acids, each of the L-form and the D-form can be used and the optical resolution is carried out using one of them.

The amount of the optically active N-acylamino acid to be used is usually from 0.5 to 1.5 moles, preferably an equimolar amount with regard to racemic N-tert-butyl-2-piperazine carboxamide.

For operating the optical resolution, a solvent is usually used. As the solvent being used, there is no particular restriction if the solvent can dissolve both racemic N-tert-butyl-2-piperazine carboxamide, and the optically active N-acylamino acid without changing the qualities of both the starting materials, and further precipitates the sparingly soluble diastereomer salt which is one of two kinds of diastereomer salts formed. As such a solvent, water, a hydrophilic organic solvent (for example, alcohols such as methanol, ethanol, n-propyl alcohol, isopropyl alcohol, etc.; ketones such as acetone, methyl ethyl ketone, etc.; ethers such as tetrahydrofuran, dioxane, etc.; acetonitrile, and N,N-diemthylformamide), or a mixture thereof is preferred.

The temperature at the case of mixing the optically active N-acylamino acid and N-tert-butyl-2-piperazine carboxamide as the racemic mixture is not higher than the boiling point of the solvent and is in the range of usually from 0° C. to 100° C., and preferably from 0° C. to 80° C. The temperature of the crystallization is preferably not higher than 50° C. for obtaining a high yield.

The diastereomer salt obtained by the crystallization is, if necessary, separated and purified by the method of a recrystallization, a reprecipitation, etc., whereby the optical purity of N-tert-butyl-2-piperazine carboxamide contained in the diastereomer salt can be further increased.

After obtaining the diastereomer salt as described above, by decomposing the salt by a proper method, optically active N-tert-butyl-2-piperazine carboxamide and the resolving agent can be isolated. For example, an aqueous solution containing the diastereomer salt is alkalified, optically active N-tert-butyl-2-piperazine carboxamide is extracted with water and a hydrophobic organic solvent, and the solvents distilled off, whereby optically active N-tert-butyl-2-piperazine carboxamide can be obtained.

The hydrophobic organic solvent to be used in the above process does not hinder the completion of the reaction and dissolves N-tert-butyl-2-piperazine carboxamide. Suitable example of the hydrophobic organic solvent are halogenated hydrocarbons such as methylene chloride, chloroform, dichloroethane, carbon tetrachloride, etc.; aromatic hydrocarbons such as benzene, toluene, xylene, etc.; aliphatic hydrocarbons such as hexane, heptane, cyclohexane, etc.; esters such as ethyl formate, ethyl acetate, propyl acetate, etc.; and ethers such as diethyl ether, dibutyl ether, etc.

As the base being used, there are, for example, alkali metal hydroxides such as sodium hydroxide, potassium hydroxide, barium hydroxide, lithium hydroxide, etc.; alkali metal carbonates such as sodium carbonate, potassium carbonate, etc.; and alkali metal hydrogencarbonates such as sodium hydrogencarbonate, potassium hydrogencarbonate, lithium hydrogencarbonate, etc.

The reaction step is carried out at a reflux temperature from 0° C. but since when the temperature is increased, there is a possibility of causing the hydrolysis and the racemization of the amide, it is preferred the step is carried out at a temperature of from 0° C. to 20° C.

After acidifying the aqueous layer formed after extracting optically active N-tert-butyl-2-piperazine carboxamide, by extracting the aqueous layer with a proper water-insoluble solvent and distilling off the solvent, an optically active N-acylamino acid can be isolated. The optically active N-acylamino acid can be re-used as the resolving agent.

Also, by separating and purifying optically active N-tert-butyl-2-piperazine carboxamide obtained using a recrystallization, a reprecipitation, or an optically active column chromatography, the optical purity thereof can be more increased.

Then, the following examples are intended to illustrate practically the present invention but not to limit the invention in any way.

EXAMPLE 1

Into 300 ml of tetrahydrofuran was added 54.1 g (0.9 mole) of ethylenediamine and the mixture was heated to 30°

C. To the mixture was added dropwise 52.5 g (0.6 mole) of 2-chloroacrylonitrile over a period of 2 hours with stirring and further stirring was continued for 6 hours. During stirring, the temperature was kept at about 30° C. The reaction mixture formed was cooled to 20° C. and precipitates formed were removed by filtration. After adding 35% hydrochloric acid to the filtrate formed to adjust pH of the mixture to 4, precipitates formed were collected by filtration. The precipitates were dissolved in 20% hydrochloric acid and the solution thus formed was added dropwise to tetrahydrofuran. Precipitates formed were collected by filtration and the solvent attaching the precipitates was removed under reduced pressure to provide 55.2 g (yield 50%) of 2-cyanopiperazine-di-hydrochloride. The analytical values of the product were as follows.

$^1$H-NMR (D$_2$O, 400 MHz): δ(ppm): 3.2 to 3.4 (4H, m), 3.57 (2H, dd, J=12.0 and 4.0 Hz), 4.72 (1H, t, J=4.0 Hz) IR (KBr): ν(cm$^{-1}$): 3400, 2905, 2655, 2409, 2143, 1529, 1430, 1340, 1290, 1071, 940, 558, 519

| Elemental Analysis: | | | |
|---|---|---|---|
| | C | H | N |
| Calculated: | 32.6% | 6.0% | 22.8% |
| Found: | 32.6% | 6.2% | 22.6% |

EXAMPLE 2

In Example 1, after adding 10% sulfuric acid to the filtrate formed by filtrating off the precipitates from the reaction mixture to adjust pH of the mixture to 4, precipitates formed were collected by filtration. The precipitates thus collected were dissolved in 10% sulfuric acid and the solution was added dropwise to tetrahydrofuran. Precipitates thus formed were collected by filtration and the solvent attached to the precipitates was removed under reduced pressure to provide 57.7 g (yield 46%) of 2-cyanopiperazine.sulfate. The analytical values of the product were as follows.

$^1$H-NMR (D$_2$O, 400 MHz): δ(ppm): 3.1 to 3.3 (4H, m), 3.47 (2H, dd, J=16.0 and 4.0 Hz), 4.51 (1H, t, J=4.0 Hz) IR (KBr): ν (cm$^{-1}$): 3405, 2935, 2590, 2460, 2135, 1602, 1477, 1439, 1137, 1098, 1060, 1015, 614

| Elemental Analysis: | | | |
|---|---|---|---|
| | C | H | N |
| Calculated: | 28.7% | 5.3% | 20.1% |
| Found: | 28.5% | 5.5% | 19.9% |

EXAMPLE 3

Into 400 ml of tetrahydrofuran was added 180.3 g (3.0 moles) of ethylenediamine and the mixture was heated to 30° C. To the mixture was added dropwise 52.5 g (0.6 mole) of 2-chloroacrylonitrile over a period of 2 hours with stirring and further stirring was continued for 6 hours. During stirring, the temperature was kept at about 30° C. After the reaction was over, when the reaction liquid was analyzed by liquid chromatography, the yield of 2-cyanopiperazine obtained was 80%. Then, after distilling off tetrahydrofuran under reduced pressure, 30% sulfuric acid was added to the residue to adjust pH to 4, precipitates formed were collected by filtration. Furthermore, the precipitates thus collected were washed with water, filtrated, and dried to provide 88.4 g (yield 67%, purity 95%) of 2-cyanopiperazine.di-hydrochloride.

EXAMPLE 4

The same procedure as in Example 3 was followed by using 72.1 g (1.2 mole) of ethylenediamine. After the reaction was over, when the reaction liquid was analyzed by liquid chromatography, the yield of 2-cyanopiperazine obtained was 60%.

EXAMPLE 5

The same procedure as in Example 3 was carried out using 360.6 g (6.0 moles) of ethylenediamine. After the reaction was over, when the reaction liquid was analyzed by liquid chromatography, the yield of 2-cyanopiperazine obtained was 65%.

EXAMPLE 6

Into 300 ml of tetrahydrofuran was added 72.1 g (1.2 mole) of ethylenediamine and the mixture was heated to 30° C. To the mixture was added dropwise 73.2 g (0.6 mole) of 2,3-dichloropropionitrile over a period of 2 hours with stirring and further stirring was continued for 6 hours. During stirring, the temperature was kept at about 30° C. The reaction mixture was cooled to 20° C. and precipitates formed were removed by filtration. After adding 10% sulfuric acid to the filtrate formed to adjust pH thereof to 4, precipitates formed were collected by filtration. The precipitates were dissolved in 10% sulfuric acid and the solution formed was added dropwise to tetrahydrofuran. Precipitates formed were collected by filtration and the solvent attached to the precipitates was removed under reduced pressure to provide 57.7 g (yield 46%) of 2-cyanopiperazine-sulfate. The analytical values of the product were as follows.

$^1$H-NMR (D$_2$O, 400 MHz): δ(ppm): 3.1 to 3.3 (4H, m), 3.47 (2H, dd, J=16.0 and 4.0 Hz), 4.51 (1H, t, J=4.0 Hz) IR (KBr): ν(cm$^{-1}$): 3405, 2935, 2590, 2460, 2135, 1602, 1477, 1439, 1137, 1098, 1060, 1015, 614

| Elemental Analysis: | | | |
|---|---|---|---|
| | C | H | N |
| Calculated: | 28.7% | 5.3% | 20.1% |
| Found: | 28.5% | 5.5% | 19.9% |

EXAMPLE 7

Into 500 ml of tetrahydrofuran was added 180.3 g (3.0 moles) of ethylenediamine and the mixture was heated to 30° C. To the mixture was added dropwise 74.4 g (0.6 mole) of 2,3-dichloropropionitrile over a period of 2 hours with stirring and further stirring was continued for 5 hours. During stirring, the temperature was kept at about 30° C. After removing tetrahydrofuran from the reaction mixture under reduced pressure, the residue was neutralized with an aqueous 30% sulfuric acid solution until pH became 1 and precipitates thus formed were collected by filtration. After suspending the precipitates thus collected in 500 ml of water, the suspension was filtered again and the residue obtained by the filtration was dried to provide 81.5 g (yield 67%) of 2-cyanopiperazine sulfate.

EXAMPLE 8

By following the same procedure as in Example 7 using 360.6 g (6.0 moles) of ethylenediamine, 75.2 g (yield 60%) of 2-cyanopiperazine sulfate was obtained.

EXAMPLE 9

Into 300 ml of tetrahydrofuran was added 54.1 g (0.9 mole) of ethylenediamine and the mixture was heated to 30°

C. To the mixture was added dropwise 52.5 g (0.6 mole) of 2-chloroacrylonitrile over a period of 2 hours with stirring and further stirring was continued for 6 hours.

During stirring, the temperature was kept at about 30° C. The reaction mixture was cooled to 20° C. and precipitates formed were removed by filtration. After adding 10% sulfuric acid to the filtrate formed to adjust pH thereof to 4, precipitates formed were collected by filtration. The precipitates were dissolved in 10% sulfuric acid and the solution was added dropwise to tetrahydrofuran. Precipitates formed was collected by filtration and the solvent attached to the precipitates was removed under reduced pressure to provide 57.7 g (yield 46%) of 2-cyanopiperazine-sulfate. The analytical values of the product were as follows.

$^1$H-NMR (D$_2$O, 400 MHz): δ(ppm): 3.1 to 3.3 (4H, m), 3.47 (2H, dd, J=16.0 and 4.0 Hz), 4.51 (1H, t, J=4.0 Hz) IR (KBr): ν(cm$^{-1}$): 3405, 2935, 2590, 2460, 2135, 1602, 1477, 1439, 1137, 1098, 1060, 1015, 614

| Elemental Analysis: | | | |
|---|---|---|---|
| | C | H | N |
| Calculated: | 28.7% | 5.3% | 20.1% |
| Found: | 28.5% | 5.5% | 19.9% |

EXAMPLE 10

In 1029 g (8.40 moles) of an aqueous 80% sulfuric acid was dissolved 219.5 g (1.05 mole) of 2-cyanopiperazine sulfate with stirring while keeping the temperature below 40° C. Then, while maintaining the temperature of from 9° C. to 15° C., to the solution was added dropwise 187 g (2.52 moles) of tert-butyl alcohol over a period of 3 hours and further, the mixture was kept at the same temperature for 2.5 hours to complete the reaction. Then, after adding 3 liters of water to the reaction liquid thus obtained, the mixture was neutralized with an aqueous solution of 25% sodium hydroxide until pH thereof became 10. Then, the reaction liquid was extracted twice with one liter of chloroform, the extracts were combined with each other, and chloroform was removed from the mixed extract under reduced pressure to provide 106.8 g (yield 55%) of N-tert-butyl-2-piperazine carboxamide having a melting point of from 151° C. to 152° C.

EXAMPLE 11

In a reaction vessel were charged 343 g of water and 389 g (5.25 moles) of tert-butyl alcohol and then 219.5 g (1.05 moles) of 2-cyanopiperazine sulfate was dissolved in the mixture with stirring while keeping the temperature below 25° C. Then, while keeping the temperature at 25° C., to the solution was added dropwise 1372 g (8.4 moles) of an aqueous 80% sulfuric acid solution and further, the temperature of the mixture was kept at 40° C. for 3 hours to complete the reaction. Then, after cooling the reaction liquid to 25° C., 2700 g of tetrahydrofuran was added to the reaction liquid and the mixture was kept at a temperature of 0° C. for 3 hours. Precipitates were collected by filtration, dried, 241 g of the precipitates thus obtained was dissolved in in 480 g of water and the solution was neutralized with an aqueous solution of 25% sodium hydroxide until pH thereof became 13. The solution was extracted thrice with one liter of chloroform, the extracts were combined with one another and chloroform was removed from the mixed extract under reduced pressure to provide 142 g (yield 73%) of N-tert-butyl-2-piperazine carboxamide.

EXAMPLE 12

In a reaction vessel were charged 515 g of water and 93.4 g (1.26 mole) of tert-butyl alcohol and 219.5 g (1.05 mole) of 2-acylpiperazine sulfate was dissolved in the mixture with stirring while keeping the temperature below 25° C. Then, while keeping the temperature at 25° C., 1544 g (12.6 moles) of an aqueous 80% sulfuric acid solution was added dropwise to the solution and further, the mixture was kept at a temperature of 35° C. for 6 hours to complete the reaction. After cooling the reaction liquid to 25° C., 1750 g of tetrahydrofuran was added to the reaction liquid and the mixture was kept at 0° C. for 3 hours. Precipitates formed were collected by filtration, dried, 233 g of the precipitate thus obtained was dissolved in 900 g of water and the solution was neutralized with an aqueous solution of 47% sodium hydroxide until pH thereof became 13. The solution was extracted four times with one liter of chloroform, the extracts were combined with one another, the chloroform was removed from the mixed extract under reduced pressure to provide 142 g (yield 73%) of N-tert-butyl-2-piperazine carboxamide.

EXAMPLE 13

After adding 35 ml of ethanol to a mixture of 0.50 g (2.70 mmoles) of N-tert-butyl-2-piperazine carboxamide as the racemic mixture and 0.81 g (2.70 mmoles) of N-benzyloxycarbonyl-L-phenylalanine (Z-L-Phe), the mixture was heated to 75° C. to form a homogeneous solution and then the solution was gradually cooled to 20° C. over a period of 3 hours. Crystals precipitated were collected by suction filtration and after washing with a small amount of ethanol, the crystals were dried under reduced pressure. The weight of the crystals was 0.20 g (30%).

Then, 160 mg of the crystals obtained were dissolved in 0.50 ml of an aqueous solution of 1N sodium hydroxide, the solution was extracted thrice with 2.0 ml of chloroform and after distilled off chloroform from the mixed extract, the residue was dried under reduced pressure to provide 53 mg (yield 87%) of optically active N-tert-butyl-2-piperazine carboxamide.

When the product was analyzed by HPLC, it was confirmed that the optical purity thereof was 84% e.e. (S-form). In addition, the optical purity of the N-tert-butyl-2-piperazine carboxamide was analyzed using an optically active HPLC column (SUMICHIRAL OA-5000, trade name, manufactured by Sumitomo Chemical Company, Limited) (and so forth).

EXAMPLE 14

To a mixture of 0.50 g (2.70 mmoles) of N-tert-butyl-2-piperazine carboxamide as the racemic mixture and 0.72 g (2.70 mmoles) of N-benzyloxycarbonyl-L-aspartic acid (Z-L-Asp) was added 9.0 ml of ethanol to form a homogeneous solution and the solution was allowed to stand for 2 hours at 20° C. Crystals precipitated were collected by suction filtration and after washing with a small amount of ethanol, the crystals were dried under reduced pressure. The weight of the crystals was 0.56 g (92%).

Then, 500 mg of the crystals obtained were dissolved in 2.5 ml of an aqueous solution of 1N sodium hydroxide, the solution was extracted thrice with 3.0 ml of chloroform and after distilling off chloroform from the mixed extract, the residue was dried under reduced pressure to provide 167 mg (yield 81%) of optically active N-tert-butyl-2-piperazine carboxamide. The analytical result by HPLC showed that the optical purity thereof was 74% e.e. (S-form).

According to the present invention, 2-cyanopiperazine or the salt thereof useful as the starting material for medicaments, agricultural chemicals, etc. can be easily produced, and also by using the 2-cyanopiperazine, N-tert-butyl-2-piperazine carboxamide can be produced at a low cost and with a good yield.

Also, according to the method of this invention, by using the inexpensive material as a resolving agent, the optical resolution of N-tert-butyl-2-piperazine carboxamide as the racemic mixture (RS) can be carried out by a simple operation and with a high yield.

While the invention has been described in detail and with reference to specific examples thereof, it will be apparent to one skilled in the art that various changes and modifications can be made therein without departing from the spirit and scope thereof.

What is claimed is:

1. A method of producing 2-cyanopiperazine represented by following formula (1):

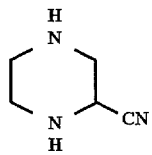
(1)

which comprises reacting an ethylenediamine with a 2-halogenoacrylonitrile represented by following formula (9):

(9)

wherein X represents a halogen atom.

2. The method as claimed in claim 1, wherein the reaction is carried out in the presence of ethylenediamine in an amount at least 1.5 times by mole as much as the amount of the 2-halogenoacrylonitrile.

3. The method as claimed in claim 1, wherein the reaction is carried out in the presence of a base.

4. The method as claimed in claim 1, wherein the halogenoacrylonitrile is 2-chloroacrylonitrile.

5. The method as claimed in claim 1, wherein the reaction is carried out in the presence of a solvent.

* * * * *